United States Patent [19]

Koenig et al.

[11] 4,294,773

[45] Oct. 13, 1981

[54] PREPARATION OF 1-HALOALKYL ISOCYANATES AND 1-ALKENYL ISOCYANATES

[75] Inventors: Karl-Heinz Koenig, Frankenthal; Karl-Heinz Feuerherd; Heinz-Guenter Oeser, both of Ludwigshafen, all of Fed. Rep. of Germany

[73] Assignee: BASF Aktiengesellschaft, Fed. Rep. of Germany

[21] Appl. No.: 175,591

[22] Filed: Aug. 5, 1980

[30] Foreign Application Priority Data

Sep. 13, 1979 [DE] Fed. Rep. of Germany ....... 2937006

[51] Int. Cl.³ ................ C07C 118/00; C07C 119/042
[52] U.S. Cl. .......................... 260/453 P; 260/453 AL
[58] Field of Search ...................... 260/453 P, 453 AL

[56] References Cited

U.S. PATENT DOCUMENTS

| | | | |
|---|---|---|---|
| 3,468,923 | 9/1969 | Koenig et al. | 260/453 AL |
| 3,535,360 | 10/1970 | Holtschmidt et al. | 260/453 P |
| 3,860,623 | 1/1975 | Zanker et al. | 260/453 P |

OTHER PUBLICATIONS

Sato, J. Org. Chem., vol. 26, pp. 770–779, (1961).
Hoover et al., J. Org. Chem., vol. 28, pp. 1825–1830, (1963).
Merrit, J. Org. Chem., vol. 32, pp. 1633–1635, (1967).

*Primary Examiner*—Dolph H. Torrence
*Attorney, Agent, or Firm*—Keil & Witherspoon

[57] ABSTRACT

1-Haloalkyl isocyanates and 1-alkenyl isocyanates are prepared by reacting 1-haloalkylcarbamic acid halides or 1-haloalkyl isocyanates with α-pinene.

The 1-alkenyl isocyanates and 1-haloalkyl isocyanates obtained according to the invention are valuable starting materials for the preparation of pest control agents, dyes, drugs, water-repellent textile finishes, detergents, plastics, bleaches and adhesives.

10 Claims, No Drawings

PREPARATION OF 1-HALOALKYL ISOCYANATES AND 1-ALKENYL ISOCYANATES

The present invention relates to a process for the preparation of 1-haloalkyl isocyanates and 1-alkenyl isocyanates by reacting 1-haloalkylcarbamic acid halides or 1-haloalkyl isocyanates with α-pinene.

It is difficult to synthesize 1-alkenyl isocyanates economically, because these compounds are very reactive; not only are they heat-labile, but they are also sensitive to acids, bases and hydrolysis. The best-known methods of preparation are the Curtius degradation of substituted acrylic acid azides (J. Org. Chem., 26 (1961), 770–779), the pyrolysis of trisvinyl isocyanurates under reduced pressure (German Published Application DAS No. 1,932,811) and the thermal cleavage of N-tert.-alkyl-N-(1-alkenyl)-carbamic acid chlorides (German Published Application DAS No. 1,922,412).

Liebigs Annalen der Chemie, 762 (1972), 88–92, and Ber., 102 (1969), 2,972–2,976, disclose the reaction of araliphatic ketimines with phosgene to give a mixture of N-chlorocarbonyl-aralkyl-ketimines and α-chloroaralkyl isocyanates. Polyhalogenated 1-haloalkyl isocyanates may be obtained by halogenating either unsubstituted or already halogen-substituted alkyl isocyanates and carbamic acid halides (U.S. Pat. No. 3,437,680 and German Laid-Open Application DOS No. 1,418,666).

1-Fluoropropyl isocyanate is obtained, alongside other reaction products, by low temperature fluorination of propyl isocyanate (J. Org. Chem., 32 (1967), 1,633–1,635).

J. Org. Chem., 28 (1963), 1,825–1,830 discloses that chloromethyl isocyanate is obtained by reacting hydroxymethyl isocyanate with thionyl chloride. 1,2,2,2-Tetrachloroethyl isocyanate may be prepared by a similar method.

We have found that 1-haloalkyl isocyantes of the formula

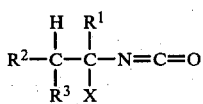

and alkenyl isocyanates of the formula

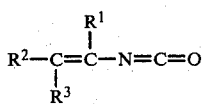

where $R^1$, $R^2$ and $R^3$ may be identical or different and each is hydrogen or methyl, and X is halogen, are obtained in an advantageous manner when a 1-haloalkylcarbamic acid halide of the formula

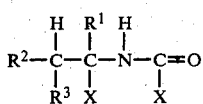

or a 1-haloalkyl isocyanate of the formula

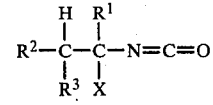

where $R^1$, $R^2$, $R^3$ and X have the above meanings, is reacted with α-pinene.

Where 1-chloroethylcarbamic acid chloride is used, the reaction may be represented by the following equation:

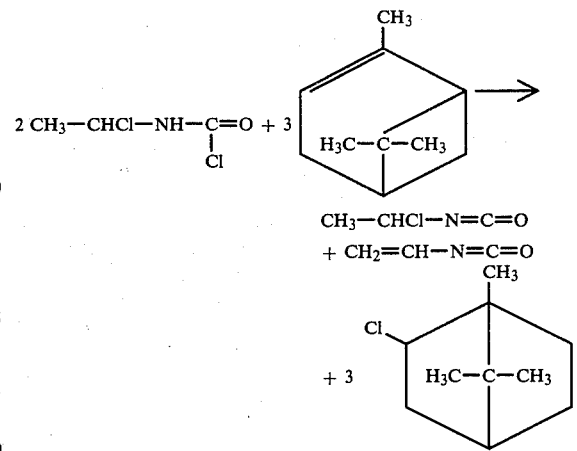

Compared to the prior art, the novel process surprisingly gives 1-alkenyl isocyanates and 1-haloalkyl isocyanates more simply and more economically, in good yield and high purity. These advantageous properties of the novel process were unforeseeable since J. Org. Chem. (loc. cit., page 1,826) discloses that chloromethyl isocyanate and chloromethylcarbamic acid chloride react readily with styrene to give an adduct which on heating gives 3-chloro-3-phenylpropyl isocyanate and cinnamyl isocyanate; similar secondary reactions of the starting material and α-pinene would have been expected. It is also surprising that in the case of α-pinene it is possible to eliminate hydrogen halide originating, not from the carbamic acid halide group but from the atoms of the carbon skeleton, with formation of an olefinic double bond. The novel process is all the more surprising since it is known that 1-alkenyl isocyanates are extremely sensitive to a hydrogen halide and form resinous polymeric substances on exposure thereto, even at room temperature (Recueil, 94 (1975), 102), whilst at very low temperatures they spontaneously undergo an addition reaction with hydrogen halide (German Laid-Open Application DOS No. 2,732,284). In view of the carbamic acid chloride/isocyanate equilibrium (Houben-Weyl, Methoden der Organischen Chemie, Volume 8, page 121) it would have been expected that any 1-alkenyl isocyanate formed would react with hydrogen halide from as yet unconverted 1-haloalkylcarbamic acid halide, to give polymeric compounds.

It is furthermore surprising that using the novel process it is possible to prepare not only 1-alkenyl isocyanates but also 1-haloalkyl isocyanates and isolate these by distillation.

As a rule, the process of preparation gives mixtures of the end products Ia and Ib. Where starting material III is used, the end product is substantially compound Ib. In the process according to the invention, α-pinene is converted to bornyl halide. Preferred starting materials II and III and accordingly preferred end products Ia and Ib are those where the radicals X in the starting material II, which may be identical or different, are advantageously bromine or especially chlorine. The starting materials II are obtained in a simple manner, for example by the process described in German Laid-Open Application DOS No. 2,741,980. The end products Ia isolated from the mixture after the reaction, for example by distillation, may be re-used as starting materials III for the reaction according to the invention, so as to obtain a high proportion of end product Ib.

Examples of suitable starting materials II are 1-chloroethylcarbamic acid chloride, 1-bromoethylcarbamic acid bromide, 1-chloropropylcarbamic acid chloride, 1-bromopropylcarbamic acid bromide, 1-chloro-1-methylethylcarbamic acid chloride, 1-bromo-1-methylethylcarbamic acid bromide, 2-chlorobut-2-yl-carbamic acid chloride, 2-bromobut-2-yl-carbamic acid bromide, 1-chloro-2-methylpropylcarbamic acid chloride, 1-bromo-2-methylpropylcarbamic acid bromide, 2-chloro-3-methylbut-2-yl-carbamic acid chloride and 2-bromo-3-methylbut-2-yl-carbamic acid bromide.

Examples of suitable starting materials III are 1-chloroethyl isocyanate, 1-bromoethyl isocyanate, 1-chloropropyl isocyanate, 1-bromopropyl isocyanate, 1-chloro-1-methylethyl isocyanate, 1-bromo-1-methylethyl isocyanate, 2-chlorobut-2-yl isocyanate, 2-bromobut-2-yl isocyanate, 1-chloro-2-methylpropyl isocyanate, 1-bromo-2-methylpropyl isocyanate, 2-chloro-3-methylbut-2-yl isocyanate and 2-bromo-3-methylbut-2-yl isocyanate.

The mixtures of end products Ia and end products Ib obtained from the reaction in general contain from 0.05 to 2 moles of Ia per mole of Ib. The higher the reaction temperature and the longer the reaction time, the higher the proportion of Ib in the final mixture. The reaction is as a rule carried out at from $-10°$ to $150°$ C.; advantageously, the reaction temperature is from $20°$ to $50°$ C. for the preparation of mixtures containing more than 1.5, especially from 1.5 to 2, moles of end product Ia per mole of end product Ib, from $70°$ to $100°$ C. for the preparation of mixtures containing from 0.5 to 1.5, especially from 0.9 to 1.1, moles of end product Ia per mole of end product Ib and from $100°$ to $150°$ C. for the preparation of mixtures containing less than 0.5, especially from 0.05 to less than 0.5, mole of end product Ia per mole of end product Ib; the reaction is carried out under atmospheric or superatmospheric pressure, continuously or batchwise. Advantageously, the reaction is started at from $-10°$ to $30°$ C. and the temperature is raised slowly, the reaction being completed at the advantageous temperatures mentioned above. The reaction time is in general from 0.5 to 6 hours; advantageously it is from 4 to 6 hours for the preparation of mixtures containing more than 1.5, in particular from 1.5 to 2, moles of end product Ia per mole of end product Ib, from 2 to 4 hours for the preparation of mixtures containing from 0.5 to 1.5, especially from 0.9 to 1.1, moles of end product Ia per mole of end product Ib, and from 0.5 to 2 hours for the preparation of mixtures containing less than 0.5, especially from 0.05 to less than 0.5, mole of end product Ia per mole of end product Ib.

The amount of α-pinene is advantageously chosen in accordance with the amount of hydrogen halide to be eliminated or the desired amount of end product Ib in the final mixture. Thus, it is advantageous to use from 2 to 20 moles of α-pinene per mole of end product Ib, preferably from 9 to 20 moles for the preparation of mixtures containing more than 1.5, especially from 1.5 to 2, moles of end product Ia per mole of end product Ib, from 4 to 9 moles for the preparation of mixtures containing from 0.5 to 1.5, especially from 0.9 to 1.1, moles of end product Ia per mole of end product Ib and from 3 to 4 moles for the preparation of mixtures containing less than 0.5, in particular from 0.05 to less than 0.5, mole of end product Ia per mole of end product Ib.

The reaction may be carried out as follows: a mixture of the starting material II or III and α-pinene is reacted at the reaction temperature for the reaction time stated above. The end products Ia and Ib are then isolated from the reaction mixture, advantageously immediately after the reaction, by raising the temperature and carrying out a fractional distillation. In place of the pure 1-haloalkyl isocyanates III or 1-haloalkyl-carbamic acid halides II it is also possible to employ the reaction mixtures obtained from the preparation of these starting materials, for example the crude halogenation mixtures resulting from the halogenation of carbamic acid halides.

The 1-alkenyl isocyanates Ib and 1-haloalkyl isocyanates Ia prepared according to the invention are valuable starting materials for the preparation of pest control agents, dyes, drugs, water-repellent textile finishes, detergents, plastics, bleaches and adhesives, since they contain an activated double bond or activated α-carbon atom in addition to a reactive isocyanate group. Furthermore, 1-alkenyl isocyanates are important monomers which can be converted to chain polymers and ladder polymers, eg. radiation-curing surface-coating resins (C.A. 51, (1975), 18694 b-e; J. Polymer Sci. 35 (1959), 215–218; J. of Coatings Techn. 49 (1977), No. 632, 82–86). They can be converted to urethanes, for example for use as foams or very flexible high molecular weight coatings, or to ureas. Regarding their use, reference may be made to the publications cited earlier and to Ullmanns Encyklopädie der technischen Chemie, Volume 9, pages 11, 12 and 404, and Volume 17, page 204 (3rd edition).

In the Examples which follow, parts are by weight.

EXAMPLE 1

A mixture of 160 parts of 1-chloroethylcarbamic acid chloride and 537 parts of α-pinene is heated at from $124°$ to $105°$ C. in the course of 2 hours, whilst stirring, and the reaction mixture is then subjected to fractional distillation. A total of 27.6 parts (23% of theory) of 1-chloroethyl isocyanate of boiling point $92°$ C./1013 mbar and 34.6 parts of vinyl isocyanate of boiling point $38.5°$ C./1013 mbar is obtained.

EXAMPLE 2

A mixture of 231 parts of 1-bromoethylcarbamic acid bromide and 475 parts of α-pinene is heated at from $23°$ to $120°$ C. in the course of 1.5 hours, whilst stirring, and the reaction mixture is then subjected to fractional distillation. A total of 14.6 parts (10% of theory) of 1-bromoethyl isocyanate of freezing point $-27.5°$ C. (decomposition) and 61.5 parts (89% of theory) of vinyl isocyanate of boiling point $38.5°$ C./1013 mbar is obtained.

We claim:

1. A process for the preparation of 1-haloalkyl isocyanates of the formula

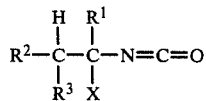

and 1-alkenyl isocyanates of the formula

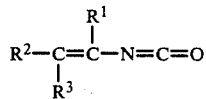

where $R^1$, $R^2$ and $R^3$ may be identical or different and each is hydrogen or methyl, and X is halogen, wherein a 1-haloalkylcarbamic acid halide of the formula

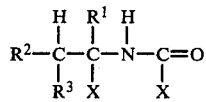

or a 1-haloalkyl isocyanate of the formula

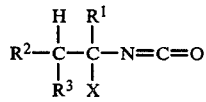

where $R^1$, $R^2$, $R^3$ and X have the above meanings, is reacted with α-pinene.

2. A process as claimed in claim 1, wherein the reaction time is from 0.5 to 6 hours.

3. A process as claimed in claim 1, wherein the reaction temperature is from −10° to 150° C.

4. A process as claimed in claim 1, wherein, for the preparation of mixtures containing more than 1.5 moles of end product Ia per mole of end product Ib, the reaction is carried out at from 20° to 50° C.

5. A process as claimed in claim 1, wherein, for the preparation of mixtures containing from 0.5 to 1.5 moles of end product Ia per mole of end product Ib, the reaction is carried out at from 70° to 100° C.

6. A process as claimed in claim 1, wherein, for the preparation of mixtures containing less than 0.5 mole of end product Ia per mole of end product Ib, the reaction is carried out at from 100° to 150° C.

7. A process as claimed in claim 1, wherein the reaction is carried out with from 2 to 20 moles of α-pinene per mole of end product Ib.

8. A process as claimed in claim 1, wherein, for the preparation of mixtures containing more than 1.5 moles of end product Ia per mole of end product Ib, the reaction is carried out with from 9 to 20 moles of α-pinene per mole of end product Ib.

9. A process as claimed in claim 1, wherein, for the preparation of mixtures containing from 0.5 to 1.5 moles of end product Ia per mole of end product Ib, the reaction is carried out with from 4 to 9 moles of α-pinene per mole of end product Ib.

10. A process as claimed in claim 1, wherein, for the preparation of mixtures containing less than 0.5 mole of end product Ia per mole of end product Ib, the reaction is carried out with from 3 to 4 moles of α-pinene per mole of end product Ib.

* * * * *